United States Patent [19]
Hogg, Walter R. et al.

[11] 3,944,917
[45] Mar. 16, 1976

[54] ELECTRICAL SENSING CIRCUITRY FOR PARTICLE ANALYZING DEVICE

[75] Inventors: Hogg, Walter R., Miami Lakes; Gerhard A. Liedholz, Miami; Wallace H. Coulter, Miami Springs, all of Fla.

[73] Assignee: Coulter Electronics, Inc., Hialeah, Fla.

[22] Filed: Aug. 13, 1973

[21] Appl. No.: 387,548

[52] U.S. Cl............... 324/71 CP; 324/30 R; 324/64
[51] Int. Cl.²...............G01N 27/00; G01N 27/42; G01R 27/14
[58] Field of Search................. 324/71 CP, 30 R, 64

[56] References Cited
UNITED STATES PATENTS

| | | | |
|---|---|---|---|
| 2,656,508 | 10/1953 | Coulter | 324/71 CP |
| 2,871,446 | 1/1959 | Wann | 324/64 |
| 3,259,842 | 7/1966 | Coulter et al. | 324/71 CP |
| 3,358,223 | 12/1967 | Birnstingl | 324/30 |
| 3,689,833 | 9/1972 | Hogg | 324/71 CP |
| 3,706,030 | 12/1972 | Klein et al. | 324/71 CP |
| 3,745,455 | 7/1973 | Haigh | 324/71 CP |

FOREIGN PATENTS OR APPLICATIONS

| | | | |
|---|---|---|---|
| 864,075 | 2/1971 | Canada | 324/71 CP |
| 274,474 | 6/1970 | U.S.S.R. | 324/71 CP |

OTHER PUBLICATIONS

Bebyakov, A.N., "Physicochemical Measurements..." USSR Journal – Izmeritel'naya Tekhnika, No. 8, Aug. 1972, pp. 58–60.
Leif, R.C. and Thomas, R.A., "Electronic Cell-Volume Analysis...", Clinical Chemistry, No. 8, Vol. 19, 1973, pp. 853–870.
"Automated Cell Identification and Cell Sorting, editing G.L. Wied and G.F. Bahr, published in 1970, pp. 139–146.
C.M.Boyd and G.W. Johnson, "Studying Zoo Plankton Populations..." Marine Technical Society of America, 1968, pp. 83–90.

Primary Examiner—Alfred E. Smith
Assistant Examiner—Rolf Hille
Attorney, Agent, or Firm—Silverman & Cass, Ltd.

[57] ABSTRACT

The electrical sensing circuitry includes a power supply and a signal-detecting circuit which are coupled through the resistance of an electrolyte in a liquid in an aperture of a particle-analyzing device between sensing electrodes positioned on either side of the aperture. The liquid containing an electrolyte and the passage of a liquidborne particle through the aperture causes a change in the resistance of the aperture thereby generating a signal which is detected by the signal-detecting circuit. The parameters of the circuit elements are chosen to provide circuit relationships which render the particle-generated signal independent of the diameter of the aperture. This is achieved by utilizing a power source having a low output impedance and a signal-detecting circuit which has a low input impedance for both D.C. and A.C., namely, at the signal frequencies of the signals sensed. The electrical circuitry also may include a conductivity monitoring circuit which may utilize one or more of the sensing electrodes and/or additional electrodes for monitoring changes in conductivity of the electrolyte and for relating these changes in conductivity to the particle-generated signals sensed by the signal-detecting circuit to alter those signals so as to render them independent of electrolyte resistivity.

30 Claims, 25 Drawing Figures

ELECTRICAL SENSING CIRCUITRY FOR PARTICLE ANALYZING DEVICE

BACKGROUND AND SUMMARY OF THE INVENTION

The present invention relates to electrical sensing circuitry for a particle-analyzing device the circuitry including circuit elements, and circuit parameters for the circuit elements, which render the output signals from the electrical sensing circuitry independent of the diameter of the aperture in the particle-sensing device and/or independent of the conductivity of the electrolyte in the bodies of liquid in the sensing device on opposite sides of the aperture so that signals generated by particles passing through the aperture are more accurately related to the size or volume of the particle.

The particle-analyzing device with which the teachings of the present invention are intended to be utilized was first disclosed in U.S. Pat. No. 2,656,508. This particle-analyzing device operated on a principle often now referred to as the "COULTER" principle. According to this principle, the passage of a microscopic particle suspended in a conducting liquid through an aperture having dimensions which approximate those of the particles, causes a change in the resistance of the electrical path through the liquid effectively contained in the aperture, if the material of the particle in the liquid had different conductivities. Studies have shown that the magnitude of this change is proportional to the volume of the particle where the cross-sectional area of the particle is smaller than the cross-sectional area of the aperture and the particle is smaller in diameter than the axial length of the aperture. This volume is the volume of actual particulate matter irrespective of the geometric configuration of the particle.

Typically, the particle-analyzing device includes a pair of electrodes each of which is positioned on either side of the aperture. An electrical power source is coupled to the electrodes and typically has had a high output impedance. A voltage sensitive signal-detecting circuit is connected across the electrodes and usually includes an A.C. coupling capacitor (D.C. blocking capacitor) so that the signal-detecting circuit will only sense changes in the voltage across the aperture caused by the passage of a particle through the aperture. These signals are commonly referred to as particle pulses and are channeled from the amplifier to other electrical circuitry for the analysis of the pulse height and for counting the pulses.

Examples of particle-analyzing devices having the structure and associated electrical circuitry described above can be found not only in U.S. Pat. No. 2,656,508 but also in U.S. Pat. Nos. 2,869,078; 2,985,830; 3,015,775; and 3,122,431.

Under proper conditions the particle-analyzing devices described above will generate electrical pulses the respective amplitudes of which are linear functions of the volume of the respective particles passing through the aperture. It is therefore a relatively simple matter to calibrate the analyzing electrical circuitry which receives the particle pulses from the signal detecting circuit. Since the initial effect of the passage of a particle through the aperture is a change of resistance, the obvious method of utilizing this change of resistance was to pass a known constant current through the resistance and detect the change of voltage which resulted. This method was so straightforward that for years no other method was considered. However, the prior art electrical sensing circuits were sensitive to changes in diameter of the aperture and to the conductivity of the liquid medium in which particles were suspended.

The conductivity of the liquid which usually contains an electrolyte is a function of composition temperature and concentration of the electrolyte in the liquid. A change in conductivity resulted in offsetting the calibration of the analyzing circuitry such that a given pulse amplitude would no longer be an accurate indication of the size of the particle generating the pulse. Various electrical sensing circuits have been proposed for providing some compensation for changes in electrolyte conductivity. Examples of these prior art circuits may be found in U.S. Pat. Nos. 3,259,842; and 3,706,030; Canadian Pat. No. 864,075; and Russian Pat. No. 274,474. Hereinafter, other electrical sensing circuits including circuitry for compensating for changes in electrolyte resistivity or conductivity are described in detail.

Even with electrical sensing circuitry which compensated for changes in electrolyte conductivity, the output signals from these circuits were still sensitive to the diameter of the aperture, often referred to as the sensing aperture. Normally, aperture diameter does not vary. However, in highly automated blood cell counters utilizing a particle-analyzing device of the type described above where the blood cell counter is utilized often, a film frequently forms on the inside surface of the aperture thus changing the effective diameter of the aperture resulting in signals which are not accurately related to the size of the blood cell passing through the aperture. This film is sometimes so thin as to be undetectable by microscope. In any event, when unexplained calibration shifts of the calibration settings for the analyzing circuitry occurred, cleaning of the aperture was resorted to in order to obtain the original calibration settings. It has also been noted that in some instances the materials used in fabricating the scanning aperture are slightly hygroscopic. An immersion in an aqueous or other electrolyte of the wafer containing the scanning aperture sometimes causes perceptible swelling of the wafer. This phenomenon also causes a change in the aperture diameter. As will be described hereinafter, the electrical sensing circuitry of the present invention provides, by proper selection of circuit elements and the parameters of the circuit elements, an advantageous and surprising result, namely, the provision of output signals from a particle-analyzing device which are essentially independent of the aperture diameter.

Also, the electrical sensing circuits of the present invention provide additional circuit elements having circuit parameters selected according to the teachings of the invention resulting in output signals which are independent of electrolyte conductivity.

According to the invention, there is provided electrical sensing circuitry for a particle-analyzing device wherein a liquid containing particles is caused to flow through a sensing aperture on either side of which is located a sensing electrode, said circuitry including, means coupled to said electrodes for establishing an electric excitation current through said aperture and means coupled to said electrodes for detecting signals generated by particles passing through said aperture, said means for establishing an electric excitation current through said aperture having a low output impedance and said means coupled to said sensing electrodes for detecting signals generated by particles passing through said aperture having a low input impedance at D.C. and at the frequencies of the particle-generated signals.

Also, according to the invention, there is provided electrical sensing circuitry for a particle-analyzing device wherein a liquid containing particles is caused to flow through a sensing aperture on either side of which is located a sensing electrode, said circuitry including means coupled to said electrodes for establishing an electric excitation current through said aperture, means coupled to said electrodes for detecting signals generated by particles passing through said aperture, and electrical monitoring means coupled to said signal-detecting means for monitoring the conductivity of the liquid containing particles and electrically for altering the output signals from said signal-detecting means relative to changes in liquid conductivity thereby to render said output signals independent of liquid conductivity.

DESCRIPTION OF THE PREFERRED EMBODIMENTS

Figure 1:
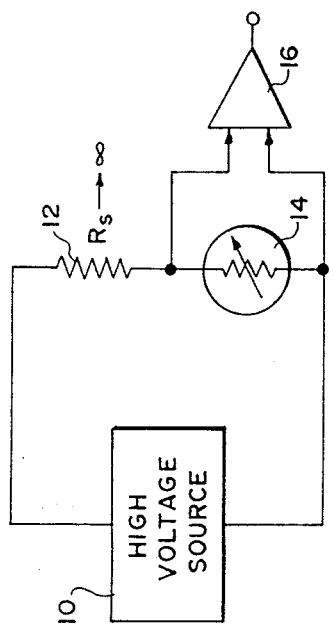
FIG. 1 is a schematic diagram of the electrical sensing circuit in a prior art particle-analyzing device.

In FIG. 1 there is illustrated a schematic diagram of a known electrical circuit used in a particle-analyzing device. Such a device is utilized for studying the physical properties of particles in a liquid. The liquid is separated into two bodies and an electrode is situated in each body of liquid. A partition separates the two bodies of liquid and an aperture is provided in the partition to permit liquid flow between the bodies of liquid. The cross-sectional extent of the aperture is relatively small and approximates the size of the microscopic particles suspended in one of the bodies of liquid. The particle-analyzing device also includes a mechanism for causing fluid flow between the bodies of liquid through the aperture. Typically, such a fluid flow causing mechanism includes a source of vacuum and control apparatus including a valve for applying the vacuum to one of the bodies of liquid for a predetermined period of time.

The electrodes in the bodies of liquid are electrically coupled to a power source and to an electrical signal-detecting circuit. It will be understood that the electrical circuit including the power source is defined in part by a current path in the bodies of liquid between the two electrodes and through the aperture. The particles in the one body of liquid have electrical conductivity which is much different than the electrical conductivity of the liquid. As a result, when particles are carried by the liquid through the aperture the particles change the impedance or resistivity of the aperture and modulate the D.C. current flowing through the aperture. This phenomena results in a change of voltage across the aperture and such changes in voltage or signals are sensed by the signal-detecting circuit which amplifies such signals and then transmits the amplified signals to other electrical circuitry wherein the signals are analyzed and studied.

The electrical circuit shown in FIG. 1 for the above-described particle-analyzing device includes a high voltage source 10, a high source resistance 12 (which may or may not be an integral part of the high voltage source 10) and a variable load resistance 14 which is the resistance across the aperture in the partition. This load resistance 14 is shown symbolically as a variable resistor enclosed by a circle in FIG. 1. The electrical signal-detecting circuit includes a high input impedance amplifier 16 which, although not shown, includes a D.C. blocking capacitor in order to prevent the diversion of aperture current into the input resistance and to prevent the relatively large D.C. component of the voltage across the aperture from saturating the amplifier 16. The high voltage source 10 and the high source resistance 12 constitute an essentially constant current supply such that the current which flows through the aperture is substantially independent of the value of the aperture resistance 14. As a particle passes through the aperture, the resistance changes by an amount ΔR and the essentially constant current flowing through the aperture and the changed resistance of the aperture results in a change of voltage across the aperture which is impressed upon the high input impedance amplifier 16.

According to Thévenin's theorem, any linear network containing one or more sources of voltage and having two terminals behaves, insofar as a load impedance connected across these terminals is concerned, as though the network and its generators were equivalent to a simple generator having an internal impedance Z and a generated voltage E where E is the voltage that appears across the terminals when no load impedance is connected and Z is the impedance that is measured between the terminals when all sources of voltage in the network are short-circuited.

Figure 2:
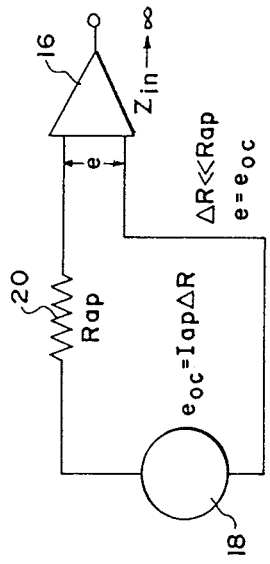
FIG. 2 is an equivalent circuit diagram according to Thévenin's theorem of the circuit shown in FIG. 1 for signals generated by particles sensed.

Utilizing Thévenin's theorem, the circuit shown in FIG. 1 can be simplified to the circuit diagram shown in FIG. 2 which includes a generator 18 with an internal impedance 20. The voltage of the generator 18 is the open circuit voltage developed in the absence of a load across the aperture and its internal impedance is the aperture resistance $R_{ap}$. Since the input impedance of the amplifier 16 is essentially infinite, it measures the open circuit voltage $e_{oc} = I_{ap}\Delta R$.

A particle-analyzing device utilizing the circuit shown in FIG. 1 can be found in U.S. Pat. No. 2,656,508. It will be noted that this circuit is dependent upon the resistance across the aperture which, in turn, is dependent upon the resistivity of the liquid or electrolyte in the aperture. The resistivity of the liquid in the aperture is dependent upon the concentration of electrolyte in the liquid and upon the temperature of the electrolyte. As a result, changes in the electrolyte concentration and temperature result in errors in the measurement of the signals generated by particles passing through the aperture. One way to alleviate this problem would be to maintain the electrolyte concentration and temperature constant. This is difficult and/or expensive to do even under laboratory conditions. Therefore, it is desirable to provide a sensing circuit for a particle-analyzing device which is independent of the resistivity or conductivity of the electrolyte or which compensates for changes in concentration and/or temperature of the electrolyte. One prior art circuit which provides for some compensation for changes in resistivity of the liquid in the aperture is disclosed in Russian Pat. No. 274,474. In that prior art patent, compensation is obtained by altering the resistance of the circuit equivalent to the source resistance 12 shown in FIG. 1 as the resistivity or conductivity of the electrolyte changes. This is accomplished by including in the resistance of the power supply circuit a resistance which is defined by a portion of the liquid. In the Russian patent, this is accomplished by inserting a third electrode into one of the bodies of liquid such that current flow from the power source first flows from a first electrode in the liquid to a second electrode in the liquid and then in the liquid through the aperture to a third electrode.

Figure 3:
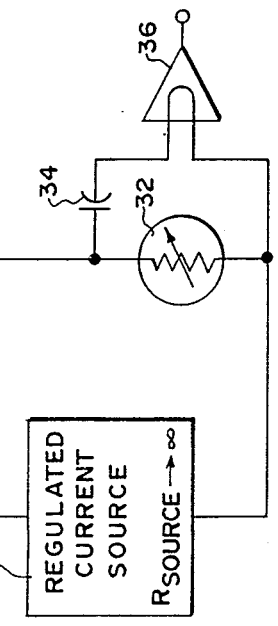
FIG. 3 is a schematic diagram of the electrical sensing circuit in another prior art particle-analyzing device.

Another prior art circuit utilized in a particle-analyzing device is illustrated in FIG. 3. For examples of a particle-analyzing device utilizing this circuit, reference may be had to U.S. Pat. No. 3,259,842. In this circuit, a regulated current source 30 having a high impedance is connected to the electrodes situated on either side of the aperture. The aperture resistance through which current from the current source flows is designated by the reference numeral 32. The signal-detecting circuit includes an A.C. coupling capacitor 34 and a low impedance amplifier 36. To better illustrate the low input impedance of the amplifier 36, the triangle symbol for the amplifier 36 includes a closed loop connecting the two inputs to the amplifier. A triangle with a closed loop between two input lines thereto is shown in other Figures of the drawings and it will be understood that such a triangle and closed loop is utilized in the drawings to emphasize the fact that the amplifier has a low input impedance for both D.C. and A.C. at the frequencies of the signals detected.

Figure 4:
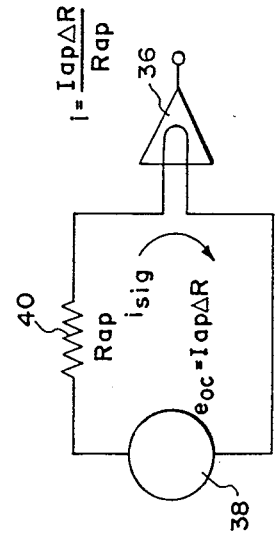
FIG. 4 is an equivalent circuit diagram according to Thévenin's theorem of the circuit shown in FIG. 3 for signals generated by particles sensed.

In FIG. 4 there is illustrated a Thévenin equivalent circuit of the circuit shown in FIG. 3 for signals detected by the signal-detecting circuit at the signal frequencies. The equivalent circuit includes a generator 38, a resistance 40, and the amplifier 36. The voltage of the generator 38 is equal to the open circuit voltage $e_{oc}$ which is equal to the product of the D.C. aperture current $I_{ap}$ multiplied by the change of resistance due to a particle flowing through the aperture, this change being ΔR. The output impedance or resistance 40 associated with the generator 38 is the aperture resistance $R_{ap}$. When a particle passes through the aperture, the open circuit voltage causes a current to flow in the signal-detecting circuit which is equal to the open circuit voltage $e_{oc}$ divided by the resistance $R_{ap}$. The amplifier 36 thus measures the short-circuit current flowing as a result of the passage of a particle through the aperture. This short-circuit current is independent of the resistivity of the electrolyte in which the particles to be studied are suspended.

Figure 6:
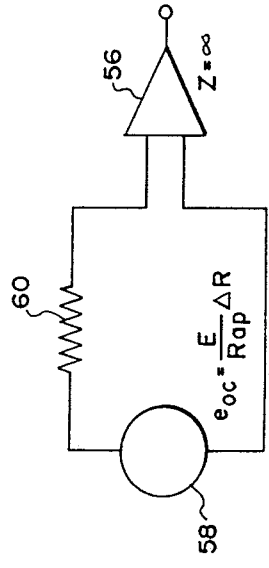
FIG. 6 is an equivalent circuit diagram according to Thévenin's theorem of the sensing circuit of FIG. 5 for signals generated by particles sensed.
Figure 5:
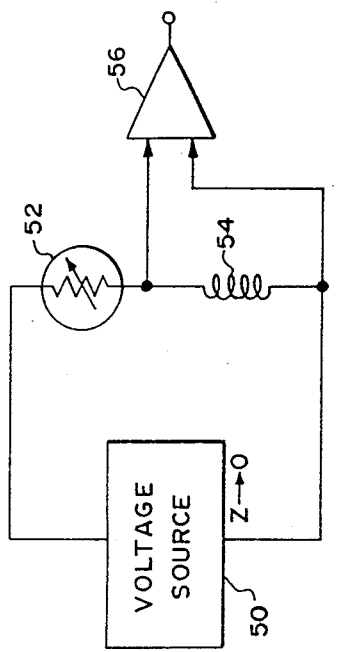
FIG. 5 is a schematic diagram of the particle-sensing circuit in still another prior art particle-analyzing device.

FIG. 5 is a simplified circuit diagram of an electrical circuit which is the electrical dual of the circuit shown in FIG. 3. A description of a particle-analyzing apparatus utilizing this circuit can be found in Canadian Pat. No. 864,075. As shown, the sensing circuit includes a low impedance high voltage source 50, an aperture resistance 52 and an inductance 54. The detecting circuit includes the inductance 54 and a high input impedance amplifier 56. The inductance 54 presents substantially zero resistance at D.C. but has a reactance at the frequency of the signals generated by particles passing through the aperture which is much higher than the aperture resistance 52 ($R_{ap}$). The Thevenin equivalent circuit at the signal frequency is shown in FIG. 6 and includes a signal generator 58 and a resistance 60 as well as the amplifier 56. The voltage of the generator 58, namely the open circuit voltage $e_{oc}$ is equal to the voltage E of the source 50 divided by the aperture resistance $R_{ap}$ (which is the temporary quiescent aperture current) multiplied by the change of resistance $\Delta R$. Again, the internal impedance of the generator 60 is the aperture resistance $R_{ap}$. Since the amplifier 56 has an input impedance which approaches infinity, resistance 60 ($R_{ap}$) has no effect and the amplifier 56 measures the open circuit voltage $e_{oc}$. As described in detail in the Canadian patent, the circuit shown in FIG. 5 is also independent of electrolyte conductivity.

Figure 7:
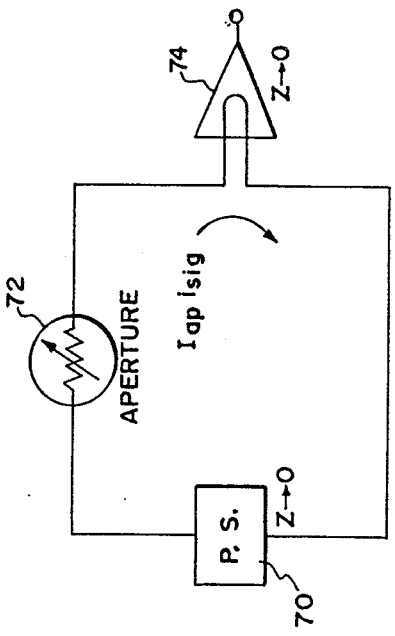
FIG. 7 is a schematic diagram of the electrical sensing circuit utilized in a particle-analyzing device constructed in accordance with the teachings of the present invention.

In FIG. 7 there is illustrated a circuit diagram of an electrical circuit utilized in a particle study device constructed according to the teachings of the present invention. In this circuit, a power supply 70 having a very low input impedance is connected in series with an aperture resistance 72 ($R_{ap}$) and a signal-detecting amplifier 74 which has a very low input impedance. The input impedance for the power supply 70 and the amplifier 74 are very low both at D.C. and at the frequencies of the signals generated by particles sensed.

Figure 8:
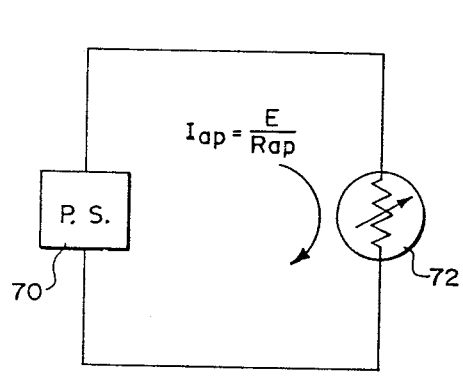
FIG. 8 is a simplified schematic diagram of the diagram shown in FIG. 7 showing the D.C. relationship between the power supply and the aperture resistance in the electrical sensing circuit.

The circuit shown in FIG. 8 is the direct current equivalent of the circuit shown in FIG. 7. Since the amplifier 74 in FIG. 7 has a negligibly small input impedance, it may be replaced by a short circuit, namely, the circuit shown in FIG. 8. It is readily obvious that the aperture current at any time is equal to the source voltage E divided by the aperture resistance $R_{ap}$. As the aperture resistance varies due to aperture geometry or electrolyte resistivity, the aperture current will vary. It should be noted however, that the changes of resistance due to particles are at most one percent of the steady state aperture resistance and may be as small as one millionth of the aperture resistance $R_{ap}$. Hence, the fact that the resistance changes due to the presence of particles passing through the aperture need not be considered here.

Figure 9:
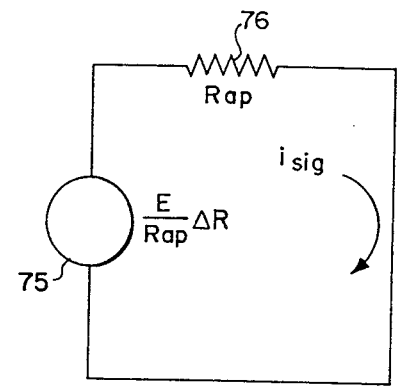
FIG. 9 is an equivalent circuit diagram according to Thévenin's theorem of the sensing circuit shown in FIG. 7 for signals generated by particles sensed.
Figure 23:
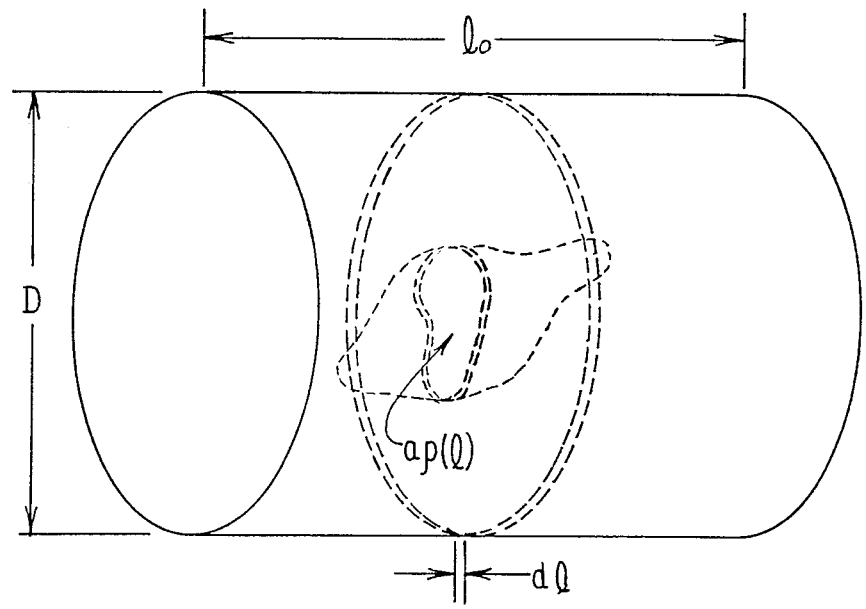
FIG. 23 is a diagram of a cylindrical volume representing an aperture in a particle-analyzing device.
Figure 24:
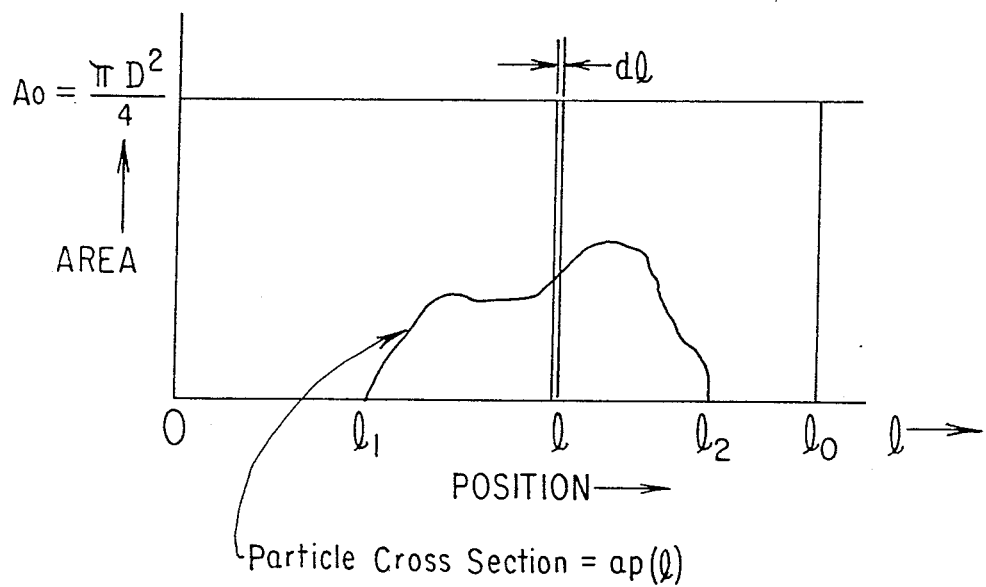
FIG. 24 is a graph of area versus position of a particle flowing through the cylindrical volume illustrated in FIG. 23.

FIG. 9 is the Thévenin equivalent circuit of the circuit shown in FIG. 7 at te frequencies of the signals generated by particles sensed. This circuit includes a generator 75 and a generator internal impedance 76. Utilizing Thevenin's theorem, the open circuit voltage, i.e., the voltage of the generator 75, is the aperture current (which is E divided by $R_{ap}$) multiplied by $\Delta R$, the change due to a particle passing through the aperture. Again, the generator internal impedance 76 is the aperture resistance $R_{ap}$. Since the amplifier 74 shown in FIG. 7, has an extremely low input impedance, it is replaced by a short circuit i.e. omitted as a series element in FIGS. 8 and 9. As a result, the useful signal is the short-circuit current $i_{sig}$ which flows as a result of a particle passing through the aperture. A mathematical analysis of $\Delta R$ and of the signal current $i_{sig}$ yields some interesting results. First of all a mathematical analysis of $\Delta R$ will be made with reference to FIGS. 23 and 24. Referring to the cyliner illustrated in FIG. 23, suppose a cylindrical volume of diameter D and length $l_o$ representing an aperture is filled with an electrolyte which has a resistivity $\rho$. The resistance $R_o$ of this volume of electrolyte in a direction parallel to its axis is $$\rho \ \frac{l_o}{\frac{\pi D^2}{4}} = \frac{4 \rho l_o}{\pi D^2}$$

or $\rho l_o / A_o$ where $A_o$ is the circular cross section area of the cylinder. This could also be thought of as an infinite series of disc-shaped resistors of length dl and area $A_o$. Thus the total resistance $R_o$ would be the sum of all of them or $$R_o = \int_o^{l_o} \frac{\rho dl}{A_o} = \frac{\rho}{A_o} \int_o^{l_o} dl = \frac{\rho l_o}{A_o} \qquad (1.)$$

Now if a particle of volume $V_p$ and of length parallel to axis ($l_2-l_1$) were placed within the "large" cylinder and a plane perpendicular to its axis were swept down its length, this plane would also cut the particle, defining a particle cross section ap. This cross section would be a complicated function of l, the distance of the plane from the reference end. The relationship between area of a particle cross section and the position of the cross section is illustrated graphically in FIG. 24.

The electrolyte in the region at the same distance from the reference end has a cross section $A_o - a_p$ which is reduced by that of the particle. Its resistance similarly can be expressed as the sum of a sequence of series connected disk or washer shaped resistors each of which has a resistance $$dR_p = \frac{\rho dl}{A_o - a_p}.$$

As before, the total resistance is the sum of all these resistances or $$R_p = \int_o^{l_o} \frac{\rho dl}{A_o - a_p} = \rho \int_o^{l_o} \frac{1}{A_o - a_p} dl \qquad (2.)$$

The signal-causing momentary change of resistance $\Delta R$ referred to above, is the difference between $R_p$ (resistance in presence of a particle) and $R_o$ (resistance in absence of a particle). Hence we have $$\Delta R = \rho \int_o^{l_o} \frac{1}{A_o - a_p} dl - \rho \ \frac{l_o}{A_o} \qquad (3.)$$

$$= \rho \int_o^{l_o} \frac{1}{A_o - a_p} dl - \rho \int_o^{l_o} \frac{1}{A_o} dl \qquad \text{from (1.)}$$

-continued $$= \rho \int_0^{l_o} \frac{1}{A_o - a_p} - \frac{1}{A_o} \, dl$$

$$= \rho \int_0^{l_o} \frac{A_o - (A_o - a_p)}{(A_o - a_p)A_o} \, dl$$

$$= \rho \int_0^{l_o} \frac{a_p}{(A_o - a_p)A_o} \, dl \quad (4.)$$

Now for most applications the maximum value of $A_p \ll A_o$. Specifically, if particle "diameter" is but 10% of aperture diameter, $A_p$ will be 1% of $A_o$, and for particle "diameters" smaller than 10% D, the quantity $A_o - a_p$ may for all practical purposes be replaced by $A_o$ giving $$\Delta R \quad \rho \int_0^{l_o} \frac{a_p}{A_o^2} \, dl = \frac{\rho}{A_o^2} \int_0^{l_o} a_p \, dl \quad (5.)$$

But $$\int_0^{l_o} a_p \, dl$$

is the volume of the particle, giving us $\Delta R \doteq P/A_o^2 \, V_p$ since p and $A_o$ are both constants we may write $\Delta R = KV_p$. This is the desired result. (7.)

It is worthy of note that no limitations have been placed on the function $A_p(l)$, thus implying that this response is independent of shape. However, the assumption was made in performing the integrations that the electric field was everywhere parallel to the axis of the aperture. In order to make these assumptions valid, $A_p(l)$ could not have any discontinuities and could at no point be multivalued. That this is the situation in an actual particle-analyzing device constructed in accordance with the teachings of U.S. Pat. No. 2,656,508 has been shown repeatedly by experiment.

Returning to the equivalent circuit shown in FIG. 9, it will be noted that since the D.C. aperture excitation current is limited only by the aperture resistance, we have
$I_{ap} = E/R_{ap}$; the Thévenin open circuit voltage developed by a particle passage is $I_{ap}\Delta R$. Signal current is likewise limited only by $R_{ap}$:

$$i_{sis} = \frac{e_{oc}}{R_{ap}} = \frac{I_{ap}\Delta R}{R_{ap}} = \frac{\frac{E}{\rho l} \cdot \rho v}{\frac{A_o A_o 2}{\rho l}} = E \cdot \frac{A_o}{\rho l} \cdot \frac{\rho v}{A_o 2} \cdot \frac{A_o}{\rho l} = \frac{Ev}{\rho l^2}.$$

which is independent of the aperture diameter D. This is very useful since the aperture length l can be measured much more accurately than the diameter D for a flat wafer in which the aperture is situated.

Figure 10:
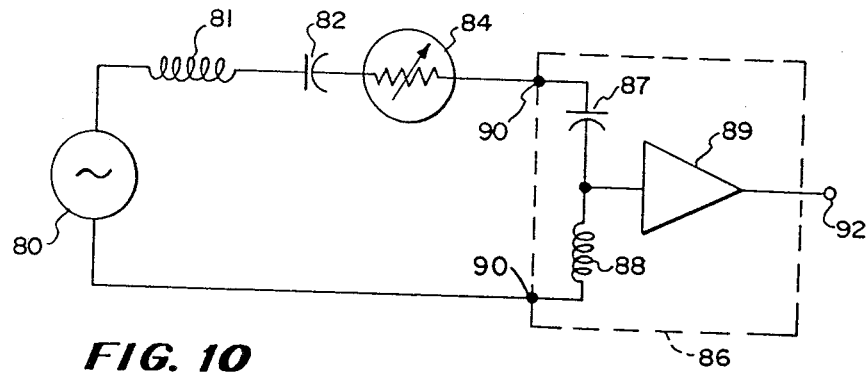
FIG. 10 is a schematic diagram of the alternating current analog of the circuit shown in FIG. 7.

In FIG. 10 there is illustrated a circuit which is the alternating current analog of the circuit shown in FIG. 7. This analog circuit includes an aperture excitation power source 80 which has a frequency in the range of 500 to 1,000 kilohertz. This frequency ensures that the sensing aperture will sense size alone. The power source 80 is connected in series with a resonant circuit comprising an inductance 81 and a capacitor 82. The source 80 is also connected in series with the aperture resistance 84 and a signal-detecting circuit 86. The signal-detecting circuit 86 also includes a series resonant circuit formed by a capacitor 87 and an inductance 88. The junction between the capacitor 87 and the inductance 88 is connected to the input of an amplifier 89 which may have a high impedance input. The capacitor 87 and the inductance 88 are arranged to be in series resonance and thus present a very low input impedance at an input terminal 90 of the signal-detecting circuit 86. The amplifier 89 measures the drop across the capacitor 87. The network comprising the inductance 88 and the capacitor 87 provide the necessary low impedance at the terminals 90, but since it is necessary to drive the high impedance amplifier 89 with a voltage, this voltage may be sensed at the junction between elements 87 and 88; hence, a network 87, 88 may thus be considered an impedance matching network between the low impedance terminals 90 and the high impedance amplifier 89. The voltage at the output terminal 92 of the amplifier 89 is thus an A.C. signal modulated by the passage of particles through the aperture but as a result of the impedance matching and the effects obtained thereby as described above in connection with the description of FIGS. 8 and 9, this modulation will be independent of the aperture diameter.

Figure 11:
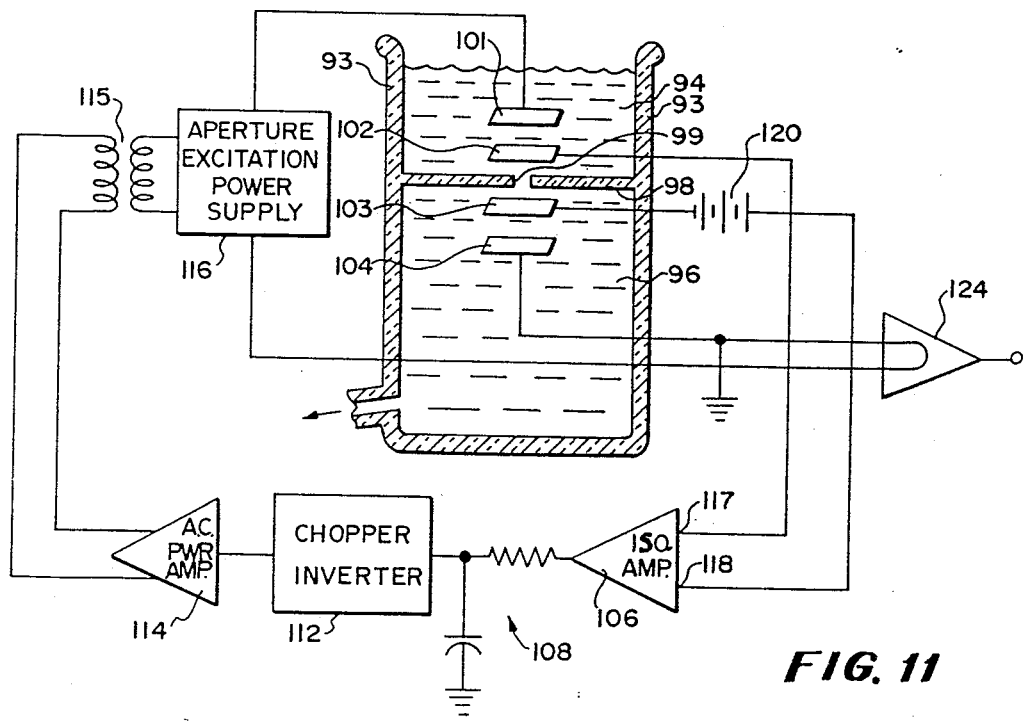
FIG. 11 is a block diagram partially in section and partially schematic of a particle-analyzing device and associated electrical circuitry constructed in accordance with the teachings of the present invention and electrically equivalent to the circuit shown in FIG. 7.

FIG. 11 illustrates a more detailed schematic diagram of a particle-analyzing device and electrical circuitry associated therewith which can be simplified to the circuit diagram shown in FIG. 7. As shown, the analyzing device includes a vessel 93 in which are contained two bodies of liquid 94 and 96 separated by a partition 98 in which there is situated a sensing aperture 99. Four electrodes, 101 – 104, are provided. The resistance between the electrodes 102 and 103 defines the aperture resistance 72 (FIGS. 7 and 8). The resistances between the electrodes 101 and 102 and between electrodes 102 and 104 are very small. Polarization voltages at the electrodes 101 and 104 are made innocuous by a feedback network comprising: an isolaton amplifier 106, an R.C. filter 108, a chopper inverter 112, a power amplifier 114, a transformer 115, and the aperture excitation power supply 116. As shown, one input 117 of the amplifier 106 is connected to the electrode 102 while the other input 118 of the amplifier 106 is connected to the positive side of a reference voltage cell 120, the other side of which is connected to the electrode 103. In this circuit, the voltage between the electrode 102 and 103 applied to the input 117 of the amplifier 106 is compared with the voltage from the voltage cell 120 applied to the input 118 of the amplifier 106. If the voltage at input 117 is different than the voltage from the voltage cell 120 applied to the input 118, an error signal will be produced by the amplifier 106. The A.C. component of this signal is filtered out by the R.C. filter 108 leaving only the D.C. component, which is then converted into A.C. by the chopper inverter 112 and then applied to the A.C. power amplifier 114. The A.C. power amplifier 114 applies A.C. power to the primary of the transformer 115. The voltage induced in the secondary of the transformer 115 is rectified and filtered in the aperture excitation power supply 116 to provide D.C. aperture excitation for the aperture 99. This is a negative feedback system and reaches equilibrium when the voltage drop across the aperture 99, that is to say between electrodes 102 and 103, equals the voltage of the reference cell 120. Any voltages which appear on the electrodes 101 and 104 will not effect the voltage across the aperture because these voltages are included in the feedback loop.

In the circuit shown in FIG. 11 the aperture excitation power supply is arranged to have a low output impedance. Also, the aperture excitation power supply is connected in series not only with the electrodes 101 and 104 but also in series with a signal-detecting amplifier 124 which has a low input impedance as shown. This circuit connection of the power supply 116, electrodes 101 and 104, and the amplifier 124 can be simplified to the circuit shown in FIG. 7. It will be noted that the electrode 104 is grounded. This permits the low impedance amplifier 124 to have a single-ended input and since the isolation amplifier 106 has an extremely high input impedance, the voltage cell 120 may be a battery as shown. Of course, if desired, an A.C. power supply may be used to provide the reference voltage. Also, it will be noted that the transformer 115 permits the aperture current excitation supply to find whatever voltage is needed in order that the voltages across the electrodes are in equilibrium.

Figure 12:
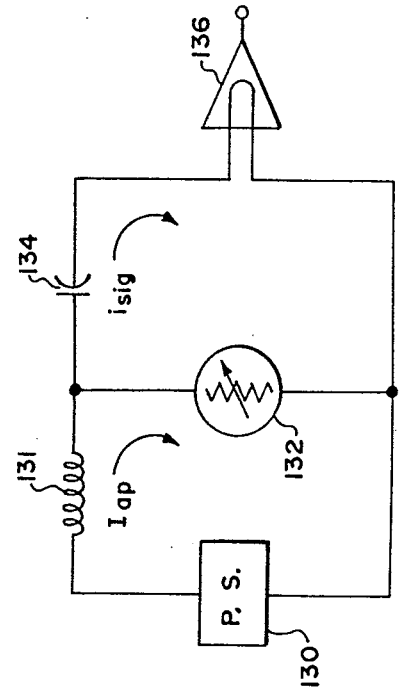
FIG. 12 is a schematic diagram of another electrical sensing circuit constructed in accordance with the teachings of the present invention.

In FIG. 12 there is illustrated a simplified schematic diagram of another circuit which produces the same result of the circuit shown in FIG. 7. This circuit includes a power supply 130 which is situated in the aperture excitation circuit which also includes an inductance 131 and the aperture resistance 132. This circuit also includes a signal-detecting circuit comprising a capacitor 134, and a signal-detecting amplifier 136 having a low input impedance. It will be apparent that the D.C. aperture current $I_{ap}$ is limited only by the aperture resistance 132 ($R_{ap}$). Considering the phenomena which occur when a signal is generated by a particle passing through the aperture at a signal frequency in the ten's of kilohertz, it will be apparent that the low impedance of the amplifier 136 effectively short-circuits the signal current, the capacitor 134 functioning as an A.C. coupling capacitor, and the high reactance of the inductance 131 prevents the signal current from flowing back into the power supply. The capacitor 134 is one which has a capacitance which results in a negligibly small reactance at signal frequencies. Since the aperture resistance is the only circuit element that limits both the D.C. aperture current and the short-circuit signal current, the equivalent circuits shown in FIGs. 8 and 9 for the circuit shown in FIG. 7 are also equivalents of the circuit shown in FIG. 12.

Figure 13:
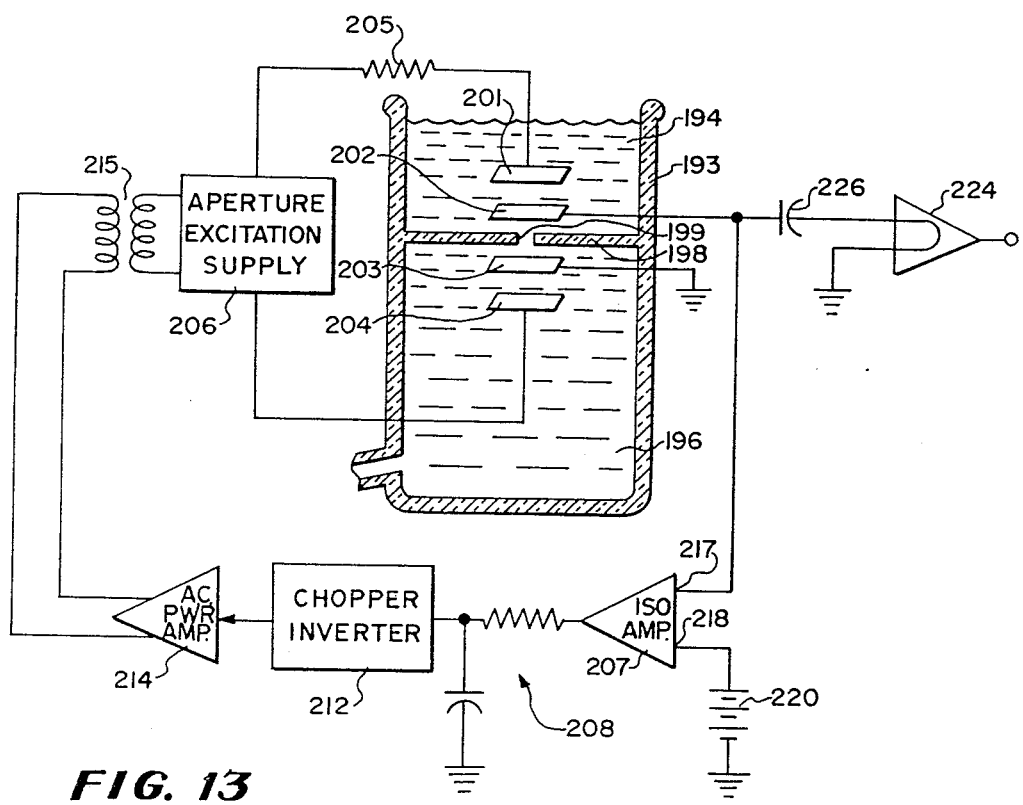
FIG. 13 is a block diagram partially in section and partially schematic of a particle-analyzing device and associated electrical circuitry constructed in accordance with the teachings of the present invention and electrically equivalent to the circuit shown in FIG. 12.

FIG. 13 is a more detailed schematic diagram of a particle-analyzing device employing a circuit which provides the circuit parameters for the circuit shown in FIG. 12 and which can be simplified to the circuit shown in FIG. 12. In the circuit shown in FIG. 13, however, the inductance 131 in the circuit of FIG. 12 is dispensed with and the voltages at the electrodes due to electrical chemical action is caused to have no influence on the circuit. The arrangement shown obviates the need to have either extremely large area electrodes or very small D.C. aperture current. It will be apparent that FIG. 13 is very similar to FIG. 11. In this respect, the particle-analyzing device includes a vessel 193 having two bodies of liquid 194 and 196 therein separated by a partition 198 in which is situated an aperture 199. Four electrodes 201 – 204 are situated in the vessel 193 and the electrodes 201 and 204 on either side of the aperture 199 are connected in series circuit relationship with a resistor 205 and an aperture excitation power supply 206. The electrode 202 is connected into a feedback circuit much the same way that the electrode 102 in FIG. 11 is connected to a feedback circuit. Again, the feedback circuit includes an isolation amplifier 207, an R.C. filter 208, a chopper inverter 212, an A.C. power amplifier 214, a transformer 215 and the aperture excitation power supply 206. As shown, the electrode 202 is connected to one input 217 of the amplifier 207. It will be noted that in this feedback circuit, the other input 218 to the amplifier 207 is connected to the positive side of a reference voltage cell 220, the other side of which is connected to the ground. Also, in this circuit, the electrode 203 is connected to ground. As a result, this circuit differs from the circuit shown in FIG. 11 by reason of the grounding of the feedback circuit. It will be apparent that the voltage across the electrodes 202 and 203 is compared with the voltage from the reference cell 220 and when the voltage across the electrodes 202 and 203 differs from the voltage in the cell 220 an error signal is generated by the amplifier 207 to cause a change in the current supplied from the power supply 206.

Again, the resistances between the electrodes 201 and 202 and between the electrodes 203 and 204 are very small. However, the aperture excitation power supply 206 is large enough to force current through the electrodes 201 and 204, and the voltage drop across the aperture is picked up by the electrodes 202 and 203. Also, as explained above, the direct current component of the voltage at the electrode 202 is coupled to the isolation amplifier 207 where it is compared with the voltage maintained by the voltage reference cell 220.

Any voltages which appear on the electrodes 201 and 204 will not effect the voltage across the aperture, the voltage across the electrodes 202 and 203, because they are included in the feedback loop. The resistance 205 serves to ensure that the aperture excitation power supply 206 has a high resistance at signal frequencies and is thus, in combination with the feedback loop, an analog to the inductance 131 shown in FIG. 12. As shown, a signal-detecting amplifier 224 has one input connected to ground and another input connected through a capacitor 226 to the electrode 202. D.C. aperture current is prevented from flowing to the amplifier 224 by the capacitor 226 which is large enough to have a neglible reactance at signal frequencies. Since the circuit shown in FIG. 13 is an all electronic or active counterpart of the simplified circuit shown in FIG. 12, the circuit shown in FIG. 13 is independent of the aperture diameter.

Figure 14:
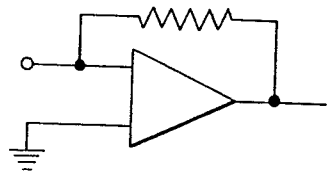
FIG. 14 is a schematic diagram of a low input impedance amplifier which may be utilized in the electrical sensing circuits constructed in accordance with the teachings of the present invention.

In FIG. 14 there is illustrated an amplifier circuit which provides a low input impedance and which therefore can be utilized in the circuits described above. Another way a low input impedance amplifier can be obtained is by utilizing matching transformers.

Although the circuits of the invention described above are not dependent upon the diameter of the sensing aperture in a particle-analyzing device, it is to be understood that there are limits on the diameter size. In this respect, it is useful to note that the circuits of the invention provide a given current density in an aperture, which density is not dependent upon aperture diameter. If one considers a change by a factor of two in the aperture diameter, one will see that the aperture cross-sectional area, and hence the resistance of the aperture, changes by a factor of four. If the size of the aperture is doubled, for instance, it will have four times the cross-sectional area and hence will have one-fourth the resistance. As a result, four times as much current will flow through the aperture. Four times the current and four times the cross-sectional area result in the same current density. However, it is important to note that the extra cross-sectional area places parallel resistance across the original aperture resistance $R_{ap}$ and injects noise current into the signal detecting amplifier. Hence, it is not possible to increase the aperture diameter without bound as a point will be reached where the noise current is greater than the signal current.

Figure 15:
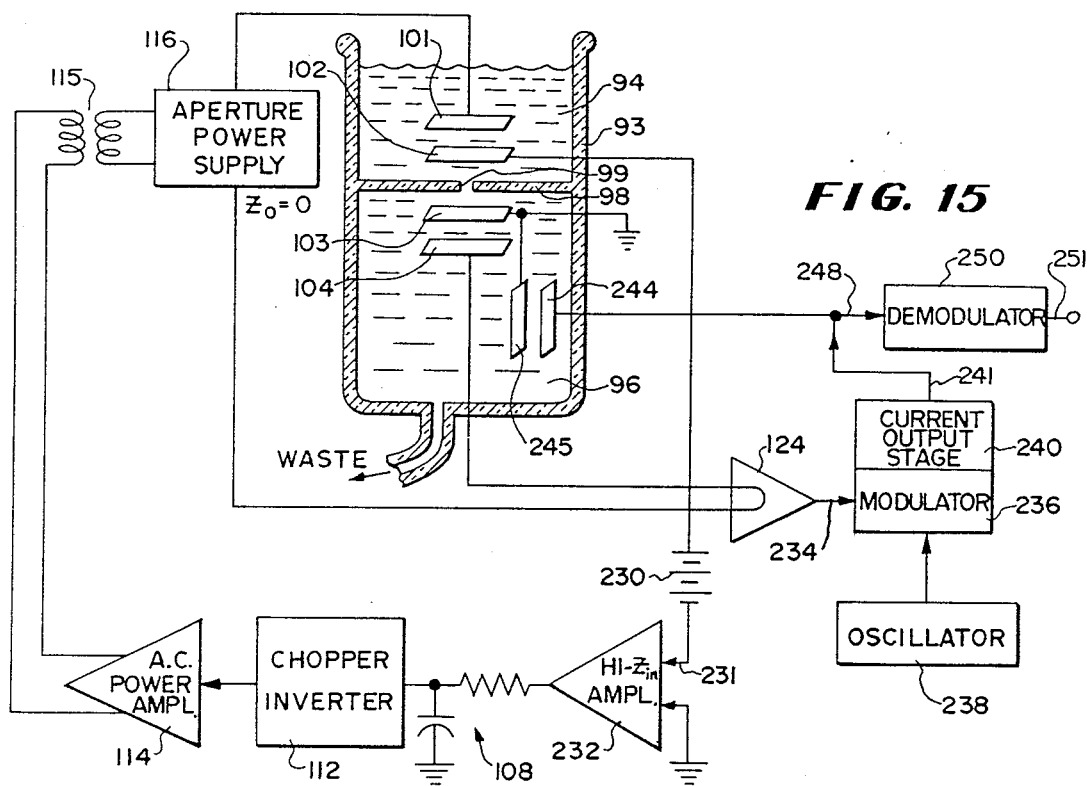
FIG. 15 is a block diagram partially in section and partially schematic of a particle-analyzing device and associated circuitry similar to the device shown in FIG. 11 and including circuitry to compensate for changes in electrolyte resistivity.

FIG. 15 illustrates a circuit similar to the circuit shown in FIG. 11 and the same reference numerals are used in FIG. 15 to designate identical structure and circuit elements. As in the circuit shown in FIG. 13, the voltage across the aperture 99 is sensed by electrodes 102 and 103. This voltage is compared with the reference voltage supplied by a battery 230 connected to the input 231 of a high input impedance amplifier 232 and, if the voltage drop across the aperture 99 differs from this reference voltage, feedback action around the loop comprising the high input impedance amplifier 232, the low pass filter 108, the chopper-inverter 112, and the A.C. power amplifier 114, will cause the aperture power supply 116 to change until the voltage drop across the aperture 99 does equal the reference voltage. It will be seen that the aperture power supply 116, the aperture power electrodes 101 and 104, the input of the low impedance amplifier 124, are all in series. Inasmuch as the only limiting resistance around this loop is that of the aperture 99, the aperture current will be inversely proportional to the aperture resistance $R_{ap}$ as in FIG. 11. However, although the signal developed at output 234 of amplifier 124 due to the passage of a particle through the aperture 99 is independent of aperture diameter, it is inversely proportional to electrolyte resistivity.

To render the signals appearing at the output 234 independent of electrolyte resistivity they are fed into a modulator 236 and used to modulate the amplitude of the voltage from an oscillator 238 connected thereto. The modulator 236 is equipped with a current or high impedance output stage 240 which has an output current proportional to the modulator carrier irrespective of the resistive load placed on the output terminal 241. Such a resistive load is established by another pair of electrodes 244 and 245 immersed in the same electrolyte. The resistance between these electrodes 244 and 245 is proportional to the distance between them and inversely proportional to their area and directly proportional to the electrolyte resistivity. For constant geometry, the distance and areas are immaterial; it is only necessary that they be stationary with respect to each other, and large enough so that inevitable inaccuracies are negligible.

The modulated current flowing out of terminal 241 flows into the resistance thus formed by the electrolyte. Since this resistance is proportional to the electrolyte resistivity, the signal on conductor 248 leading to demodulator 250, other things being equal, is also proportional to the resistivity. However, the signal at the output 234 was inversely proportional to the electrolyte resistivity so that the net input to the demodulator 250 does not change when the resistivity has changed, hence providing pulses at the output terminal 251 of the demodulator 250 which are independent both of aperture diameter and electrolyte resistivity, as desired.

Figure 16:
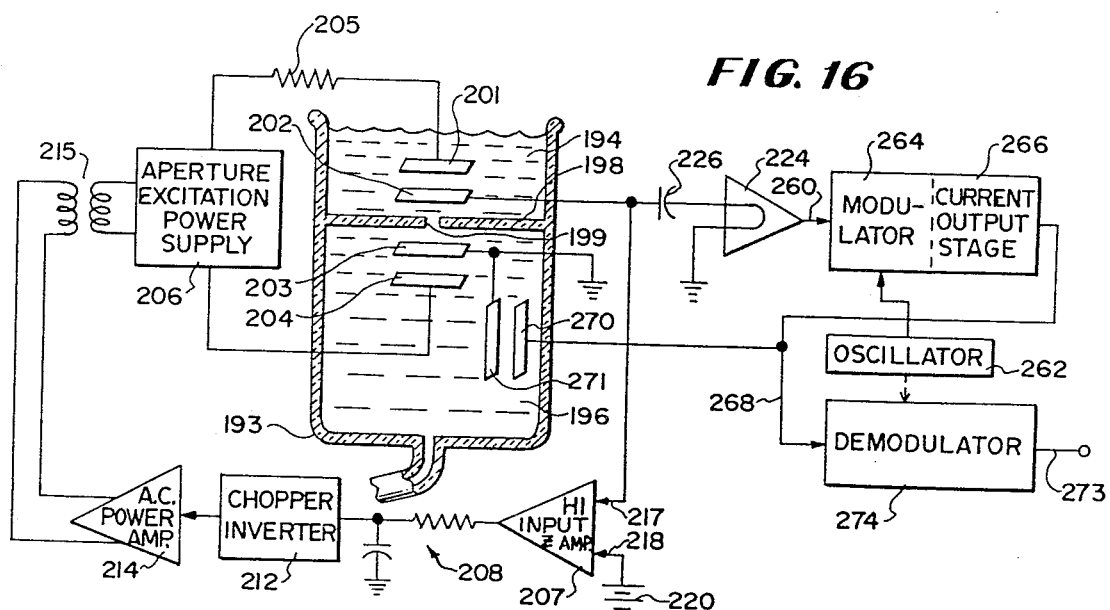
FIG. 16 is a block diagram partially in section and partially schematic of a particle-analyzing device and associated circuitry similar to the device shown in FIG. 13 and including circuitry to compensate for changes in electrolyte resistivity.

In FIG. 16 is illustrated a circuit similar to FIG. 13 and the same reference numerals are used to designate identical structure and circuit elements. In this circuit D.C. currents are blocked from flowing into the amplifier 224 of the signal detecting circuit as explained above in connection with the description of FIG. 13. This is possible if the aperture excitation power supply 206 has high impedance at signal frequencies. This high impedance is provided as shown by the isolating resistance 205. Again, the power electrodes 201 and 204 are separated from the signal electrodes 202 and 203, in order that electrochemically generated voltages do not upset the inverse relationship between the aperture current and the aperture resistance. The A.C. components of the aperture current, which are the signal currents, are short-circuited by the low impedance amplifier 224 and provide output pulses at output terminal 260 which are independent of aperture diameter but dependent upon electrolyte resistivity. Specifically, they are again inversely proportional to electrolyte resistivity for a given particle size. An oscillator 262, a modulator 264, and its current output stage 266, operate in the same manner as oscillator 238 and modulator 236 shown in FIG. 15, and cause the signal on channel 268 which is affected by the resistance across electrodes 270 and 271 to vary directly proportional to electrolyte resistivity. This, as before, causes cancellation of the two types of changes. Signals at output terminal 273 of demodulator 274 are again independent of both aperture diameter and electrolyte resistivity.

The purpose of using a high frequency carrier and a modulator is to prevent the feedback which would otherwise take place since the conductivity sensing electrodes 270 and 271 are in the same body of fluid as the detecting electrodes 202 and 203. This operation is somewhat like the reflex receivers of the early days of radio.

Figure 17:
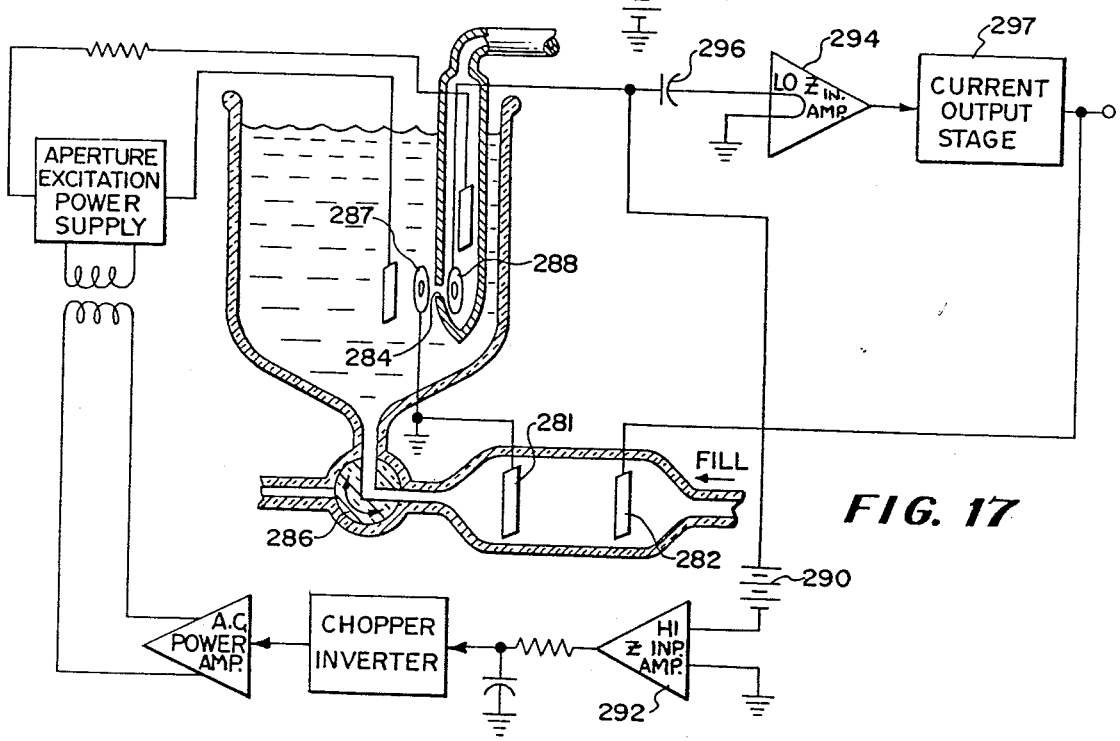
FIG. 17 is a block diagram partially in section and partially schematic of another particle-analyzing device and associated circuitry in which the sensitivity of the signal-detecting circuit is made proportional to the electrolyte resistivity without recourse to high frequency carrier modulation.

The circuit shown in FIG. 17 solves the problem of feedback by means of physical isolation between a "conductivity cell" comprising electrodes 281 and 282 and the sensing zone through aperture 284. The aperture tube sample bath configuration shown can be constructed according to the teachings of U.S. Pat. No. 3,567,321. Since the flow path for the electrolyte is interrupted by a valve 286 and sensing electrode 287 (of sensing electrodes 287 and 288) on the conductivity cell side of the aperture 284 is grounded as is the conductivity cell electrode 281 closest to the valve 286, the danger of signal feedback is neglible and the resort to a carrier frequency is unnecessary. One drawback of this arrangement is the remoteness of the conductivity cell and the possibility of temperature differences between the electrolyte in the aperture 284 and the electrolyte in the conductivity cell. This is usually not a problem, however.

The voltage across the aperture resistance is maintained by a feedback circuit which is substantially identical to the feedback circuits shown in FIGS. 15 and 16. Notice, however, that the reference voltage is provided by a reference voltage cell 290 which is connected between the sensing electrode 288 and the input of a high impedance amplifier — comparator 292 of the feedback loop, which obviates the need for a high common mode rejection in the amplifier 292. The reference voltage cell 290 can, however, be placed in either input lead to the amplifier 292 and placing the reference voltage cell 290 in the other lead in FIG. 17 permits one side of the reference voltage cell to be grounded. The choice of location of the reference voltage cell 290 is dependent upon practical considerations such as insulation resistance, hum, and noise pickup. Since the amplifiers 207 in FIG. 16 and 292 in FIG. 17 each have extremely high input impedance in order to minimize polarization problems at the sensing electrodes 202, 203 or 287, 288 the reference voltage cell 220 or 290 may constitute a battery as shown.

As in FIG. 16, the signal-detecting circuit of FIG. 17 includes a low input impedance amplifier 294 and an A.C. coupling capacitor 296. The output from the amplifier 294 is supplied to a current output stage 297 and the output from the current output stage 297 is affected as desired by the resistance across the electrodes 281, 282 of the conductivity cell.

Figure 17A:
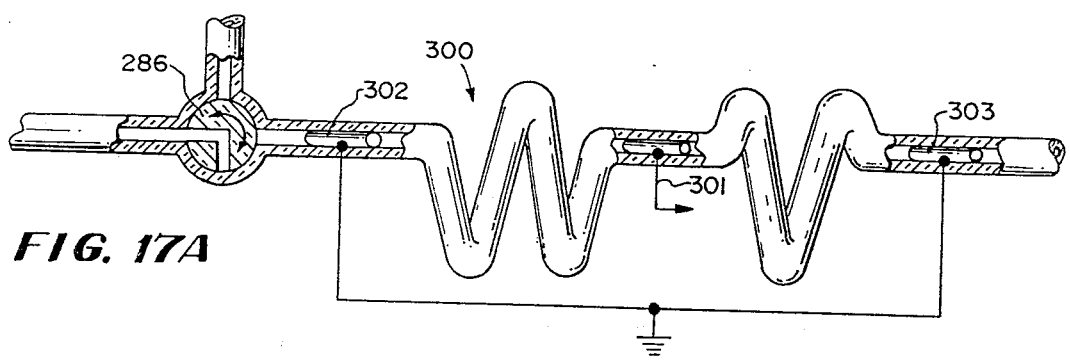
FIG. 17A is a side view partially in section and with portions broken away of a conductivity cell which can be used as an alternative to the conductivity cell shown in FIG. 17.

The conductivity cell defined by the electrodes 281 and 282 can be replaced by a long, narrow conductivity cell such as the cell 300 shown in FIG. 17A. Here the electrodes 281 and 282 are replaced by electrodes 301, 302, and 303. The electrode 301 is centrally located between the other two electrodes 302 and 303 and hence the resistance which is to be sensed and which controls the sensitivity of the signal-detecting circuit is the parallel resistance of the path between electrodes 301 and 303 and between electrodes 301 and 303. The sections of the tubing between these electrodes is shown coiled to provide higher resistance which is more convenient for the electronic circuitry utilized. The main object, however, is to provide two electrodes 302 and 303 which are both at ground potential so that any voltages induced in the connecting tubing are shorted out to ground and do not induce signals on electrode 301. Also, it will be noted that in FIG. 17A valve 286 is shown in an "Off" position.

Figure 18:
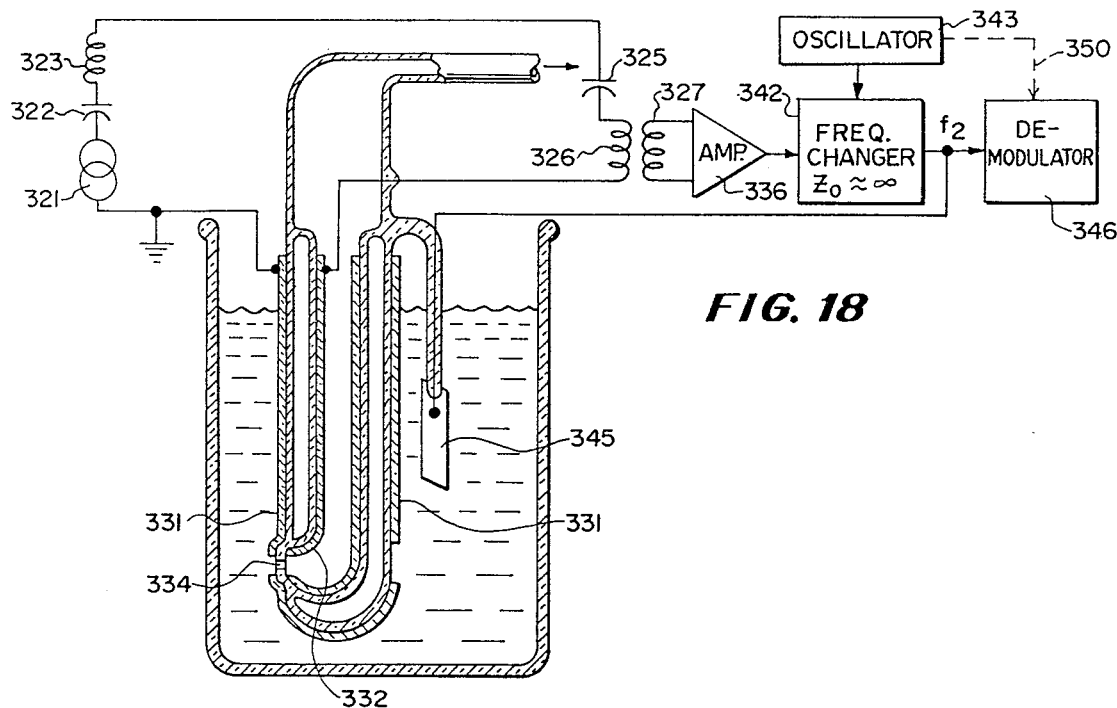
FIG. 18 is a block diagram of an all A.C. circuit arrangement in a particle-analyzing device which achieves the same results as the circuitry shown in FIG. 15.

In FIG. 18 there is illustrated a particle-analyzing device with an electrical circuit which impresses high frequency alternating current excitation across the aperture in the sensing zone of the device. This high frequency excitation is provided by an oscillator 321 which, in conjunction with a capacitor 322 and an inductance 323, provides a series tuned output impedance. In this way the power supply comprising oscillator 321, capacitor 322 and an inductance 323 form a low impedance power supply (as desired for the circuit shown in FIG. 12). The power source thus formed is series-connected, via a capacitor 325 and an inductance 326 which is part of a transformer 327, with the aperture resistance across sensing electrodes 331 and 332. These electrodes 331 and 332 are designed to come very close to the aperture 334 in a manner as disclosed in U.S. Pat. No. 3,714,565.

The capacitor 325 and the inductance 326 form a series resonant circuit such that the signal-detecting amplifying circuit formed by the transformer 327 and amplifier 336 have low impedance at the carrier frequency. It will, of course, be obvious to those skilled in the art that the capacitor 322 and the capacitor 325 as well as the inductances 323 and 326 may be lumped together to provide the same operation with fewer parts. Also, other connections are possible which will yield equivalent results. The criteria which must be met by any connection of circuit elements has been described above in connection with the description of FIGS. 7 and 12. Simply stated, this criterion is that both the generator of aperture excitation current and the amplifier in the signal-detecting circuit must have low impedance both at the carrier frequency and at the frequencies encompassed by the side bands generated by signals resulting from particles flowing through the aperture 334. The latter criterion demands that the "Q" or figure of merit of these resonant circuits be low enough to obtain the requisite bandwidth which in a known particle-analyzing device lies in the general range of 200 kilohertz total bandwidth (100 kHz on each side of the carrier frequency).

The amplifier 336 must have a broad enough passband to encompass all the signal frequencies as well. The output from the amplifier 336 is applied to a frequency changer 342 which is also driven by an oscillator 343. The oscillator 343 oscillates at a higher frequency than does the aperture current excitation oscillator 321. As a result a difference frequency appears at the output of the frequency changer and is designated $f_2$. The frequency changer 342 is designed to have a very high output impedance so that the resistance of a conductivity cell formed by electrode 331 and an auxiliary electrode 345 is small by comparison. The conductivity cell resistance between electrodes 331 and 345 will cause the output voltage from the frequency changer 342 to be proportional to the resistivity of the electrolyte and this relationship will cancel the inverse relationship to electrolyte resistivity sensed by the amplifier 336. The pass band about the beat frequency $f_2$ now contains the side bands which contain the particle size and number information which are recovered by a demodulator 346. Again, if $f_2$ is chosen to be high and the resistivity of the electrolyte is high, it may be necessary for the demodulator 346 to be a phase-sensitive demodulator in which case a phase reference signal will be necessary and can be provided from the oscillator 343 via connection 350 shown in dashed lines in FIG. 18. This will make the system sensitive only to the resistive component of the impedance of the conductivity cell formed by electrodes 331 and 345.

Figure 19:
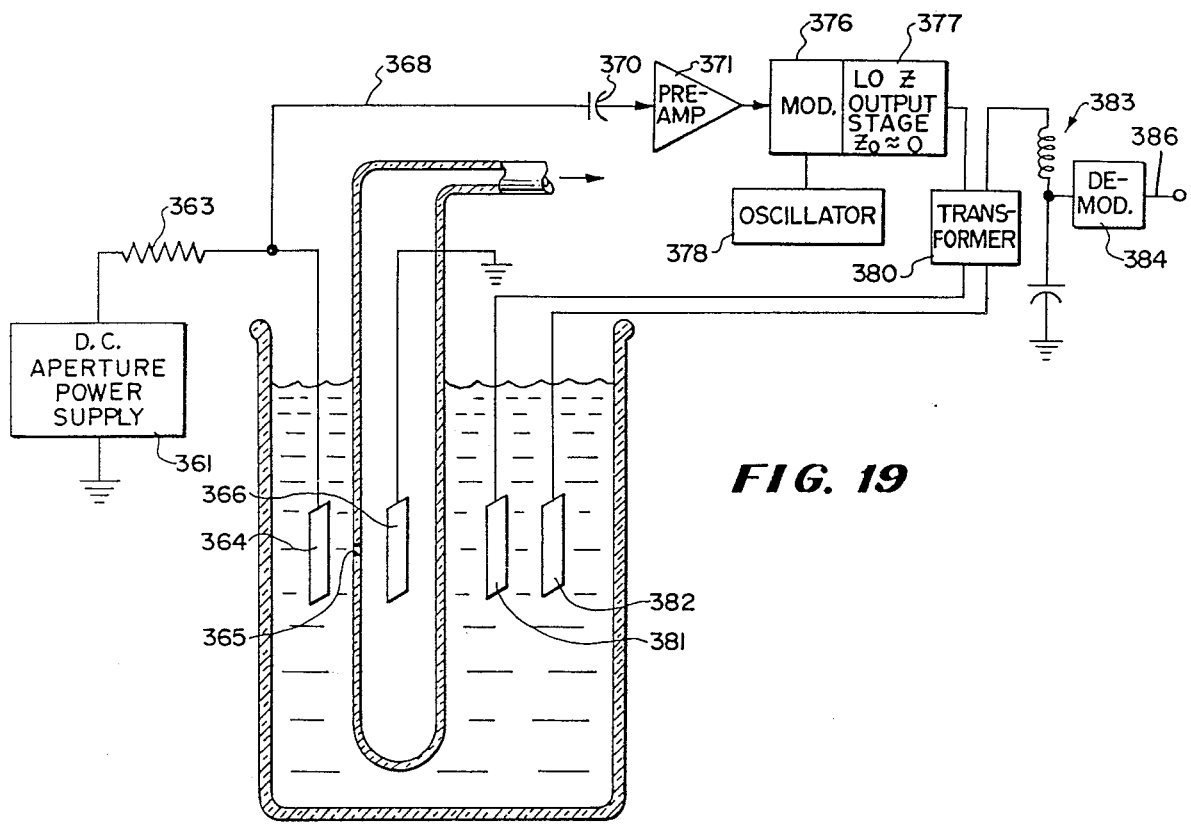
FIG. 19 is a block diagram partially schematic and partially in section of a particle-analyzing device and associated circuitry in which independence of resistivity changes is achieved by means of a high frequency carrier and modulator.

In FIG. 19 there is illustrated a particle-analyzing device which includes a D.C. aperture power supply 361 having an internal impedance 363 which, for all practical purposes, can be considered infinite. The power supply supplies current to a particle-sensing circuit including an electrode 364, a current path through aperture 365 and an electrode 366 which then flows to ground. Signals generated by particles passing through the aperture 365 are picked up by conductor 368 which is connected to the electrode 364 and passed through an A.C. coupling capacitor 370 to a preamplifier 371, the input impedance of which is for all practical purposes infinite. The output of the preamplifier 371 is applied to a modulator 376 having a low impedance output stage 377. The modulator 376 also receives high frequency energy from an oscillator 378. As shown, the low impedance output stage 377 is also coupled through a transformer 380 to a conductivity cell defined between electrodes 381 and 382. The output of the output stage 377 is connected through the transformer 380 to a series circuit 383 which is designed to present very little impedance to the output from the output stage 377. As a result, the primary of the transformer 380 connected between the output stage 377 and the series circuit 383 is the only element which limits the amount of signal current that is imposed upon the carrier frequency flowing through the output circuit to the demodulator 384. The secondary of the transformer 380 is loaded by the conductivity cell formed by the electrodes 381 and 382 and, as is well known in the art, the resistance of the conductivity cell is reflected into the primary of the transformer 380, by a factor which is the square of the turns ratio of the transformer 380. The transformer 380 also performs the dual function of isolating electrodes 381 and 382 from ground in order to avoid short-circuiting the D.C. aperture current from electrode 364. The series circuit 383 also operates as an impedance transforming device such that the demodulator 384 may be designed to have a conveniently high input impedance. All signals which appear at the output terminal 386 of the demodulator 384 are independent of electrolyte resistivity by reason of the circuit elements and circuit connections shown in FIG. 19.

It should be noted that the conductivity cell formed by the electrodes 381 and 382 is in series between a low impedance generator and a low impedance signal-detecting circuit whereas in the previous circuits exhibiting independence of aperture diameter, the conductivity cell was in shunt relationship to ground. This is necessary because in the previous circuits which are insensitive to aperture diameter, the output signals were inversely proportional to resistivity whereas in the electrical circuits of the prior art particle-analyzing devices, the output signals are directly proportional to electrolyte resistivity.

Figure 20:
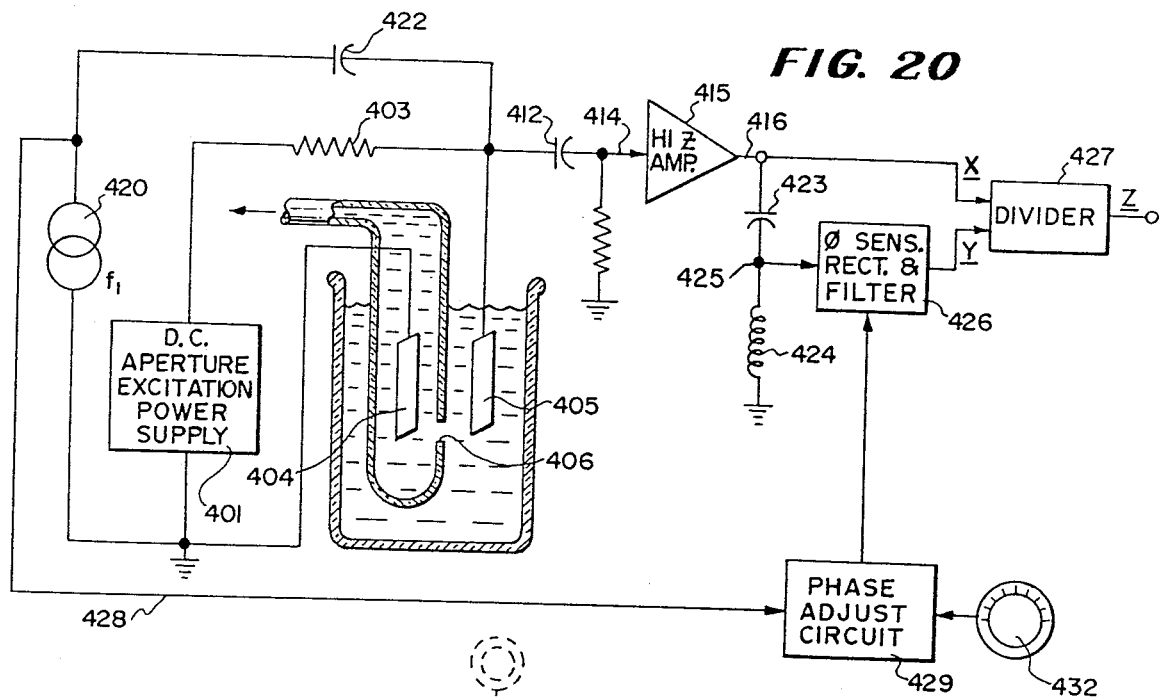
FIG. 20 is a schematic block diagram of another circuit which compensates for changes in electrolyte resistivity in a particle-analyzing device and in which the electrodes of the device serve a double function and the gain control of the signal-detecting amplifier is accomplished by means of an analog divider.

In FIG. 20 is illustrated another circuit arrangement using using D.C. aperture excitation. As shown, a power supply 401 with an internal resistance 403 is connected to electrodes 404 and 405 situated on either side of a sensing aperture 406. The resistance 403 limits the aperture current through the aperture 406 in the same manner as in the prior art circuits described above. D.C. produced pulses are picked off by a blocking capacitor 412 and applied via conductor 414 to a high impedance amplifier 415. Amplified pulses appear at the output 416. The electrodes 404, 405 also form the conductivity cell which is coupled to a conductivity sensing oscillator 420 through a coupling capacitor 422. A capacitor 423 and an inductance 424 are connected to the output 416 of the amplifier 415 as shown. The capacitor 423 and inductance 424 are series-tuned at the frequency of the conductivity sensing oscillator 420. The impedance of the series-tuned circuit in the D.C. to 100 kilohertz spectrum of the frequencies for the particles sensed appears as simply the capacitance of the capacitor 423 and hence has negligible shorting effect on the signal at the output 416. The capacitor 422 is chosen to be very small so as to have a very high reactance at the oscillator frequency $f_1$ of the oscillator 420. Simultaneously, as signals are being produced at the electrode 405, the carrier frequency voltage at electrode 405 is being modulated by the aperture resistance $R_{ap}$. The high impedance amplifier 415 has a very broad band and passes both the D.C. generated signals and the sensing frequency $f_1$. The tuned circuit comprising capacitor 423 and the inductance 424 shorts out the carrier frequency from the output 416 and a considerably higher voltage is developed at the junction 425 between capacitor 423 and inductance 424. This high frequency voltage at the junction 425 is rectified by a phase-sensitive rectifier 426 and used to drive the Y or denominator input of a voltage divider 427, the output terminal 416 being connected to the X or numerator input of divider 427. As shown, the output from the oscillator 420 is fed via a conductor 428 to a phase adjust circuit 429 which applies a reference voltage to the phase-sensitive rectifier and filter 426. The filter removes signal frequency components and applies only the quasi-steady state voltage to the Y or denominator input. The phase may be adjusted by a knob 432 by any one of several methods known to those skilled in the art such that the phase-sensitive rectifier filter 426 responds only to resistance changes at the electrode 405 and not to capacitive changes.

Since in the prior art circuits the signal developed was proportional to the electrolyte resistivity, it is necessary to compensate for changes in electrolyte conductivity such that the overall signal detector circuit gain is inversely proportional to aperture resistance. This is accomplished by means of the divider 427. The operation is as follows. A particle is sensed as it passes through the aperture 406. If the aperture resistance is doubled, the signal developed at the electrode 404 will also double but, by the same token, the high frequency-sensing voltage provided by the oscillator 420 will also double. Therefore, both the X and Y inputs to the divider 427 will double and the output from the divider 427 will remain unchanged.

Figure 21:
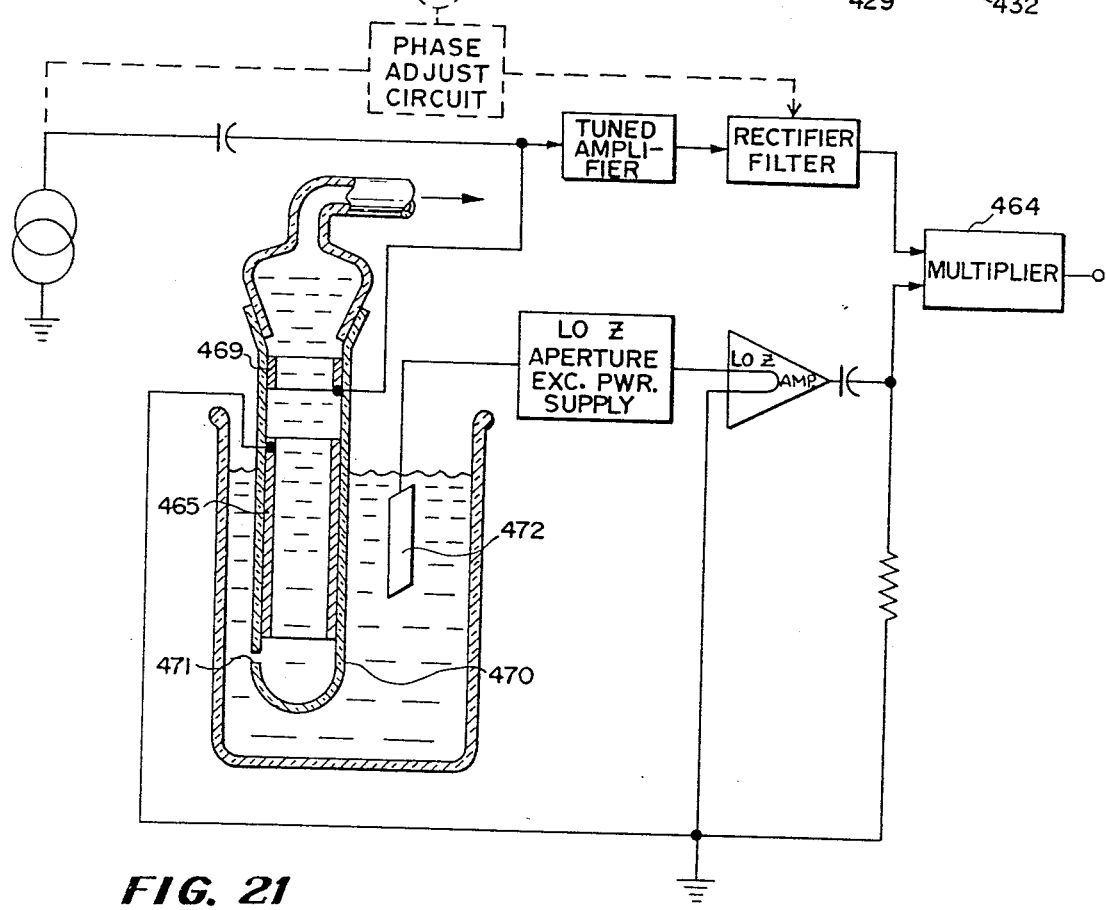
FIG. 21 is a schematic block diagram of another circuit which compensates for changes in electrolyte resistivity in a particle-analyzing device and in which the sensitivity of the signal-detecting amplifier is varied by means of a multiplier which receives correction signals carried by a high frequency carrier.

In FIG. 21 there is illustrated another circuit which provides the same type of compensation for changes in electrolyte conductivity as provided by the circuit shown in FIG. 20. This circuit also provides an output signal which is independent of aperture diameter. This circuit operates in a manner similar to the operation of the circuit in FIG. 20 but, since the initial response to a particle sensed is inversely proportional to the electrolyte resistivity, it is necessary to use a multiplier 464 instead of the divider 427 shown in FIG. 20. Also, a different electrode structure is utilized and consists of two coaxial electrodes 465 and 469 which are positioned within a tube 470 having an aperture 471 therein. The electrodes 465 and 469 are fixed to the inner wall of the tube 470.

It will be apparent from FIG. 21 that the circuitry for compensating for changes in electrolyte conductivity resistivity is substantially identical to the circuitry provided for this purpose in FIG. 20. Also, the circuitry for providing excitation current through the aperture 471 between a sensing electrode 472 and the electrode 465 is substantially identical to the sensing circuit shown schematically in FIG. 7 which provides an output signal independent of aperture diameter. This signal is applied to the multiplier 464 as is he signal for compensating for changes in electrolyte conductivity.

It is to be remembered that in all embodiments where there is compensation or changes in electrolyte conductivity, although any configuration will be acceptable, the geometry of the conductivity cell must be stable.

Figure 22:
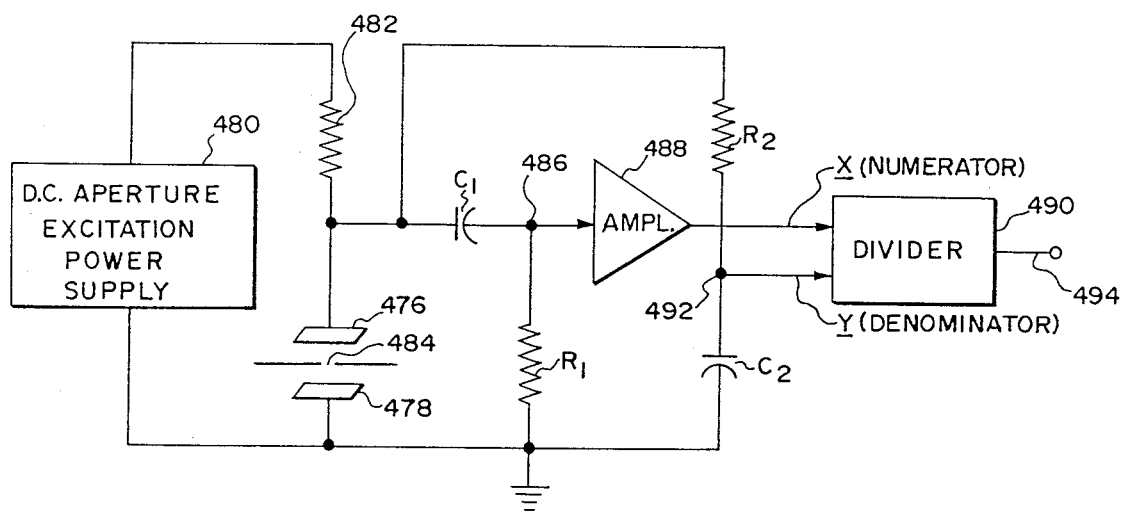
FIG. 22 is a schematic diagram of still another circuit which compensates for changes in electrolyte resistivity in a particle analyzing device.

In FIG. 22 there is illustrated another circuit for compensating for changes in electrolyte conductivity. This circuit includes sensing electrodes 476 and 478 which are supplied with excitation power from a power supply 480 through a high resistance 482. The aperture is indicated schematically by the reference numeral 484 between the electrodes 476 and 478. As in the other prior art circuits described above, the resistance 482 is much higher than the aperture resistance between the electrodes 476 and 478. The signal-detecting circuit comprises a capacitor resistance circuit $C_1, R_1$ connected across the electrodes 476 and 478. As shown, junction 486 between capacitor $C_1$ and resistor $R_1$ is connected to a signal-detecting amplifier 488 and the output from the amplifier 488 is connected to the X input of a divider 490. When a particle passes through the aperture 484 and an A.C. signal is generated, it is passed through the capacitor $C_1$ and picked up by the amplifier 488 where it is amplified and then applied to the numerator or X input of the divider 490. Compensation for changes in electrolyte conductivity is provided by a resistance capacitor circuit $R_2, C_2$ which is also connected across the electrodes 476 and 478. The capacitor $C_2$ charges to the voltage across the electrodes 476 and 478 and junction 492 between resistor R2 and capacitor C2 is connected to the Y or denominator input of the divider 490. Stated otherwise, the D.C. component of the voltage across the electrodes 476 and 478 is picked off by the resistance capacitor circuit $R_2, C_2$ and applied to the denominator input of the divider 490. Assuming the electrodes 476 and 478 are large and/or the aperture current is small so that negligible polarization voltages appear on the electrodes 476 and 478, both the D.C. component and the signal component of the voltage across the aperture 484 are proportional to aperture resistance and hence electrolyte resistivity. Thus, for example, if the resistivity is doubled, the signal will double but twice the voltage is applied to the denominator input of the divider 490 and the "Gain" of the divider will be cut in exactly half. As a result there is no change in the signal appearing at the output 494 of the divider 490 as desired.

It will be apparent from the foregoing description that the present invention provides a number of circuit embodiments which compensate for changes in electrolyte conductivity or resistivity and/or changes in aperture diameter and that such compensation circuits can take various forms to provide output signals for particle-analyzing device which are more accurate and independent of electrolyte conductivity and/or aperture diameter. Accordingly, the scope of the present invention is only to be limited by the accompanying claims.

We claim:

1. Electrical sensing circuitry for a particleanalyzing device wherein liquid containing particles is caused to flow through a sensing aperture on either side of which is located a sensing electrode, said circuitry being independent of slow changes in aperture diameter and including constant voltage means coupled to said electrodes for establishing an electric excitation current through said aperture and means coupled to said electrodes for detecting signals generated by particles passing through said aperture, said means for establishing an electric excitation current through said aperture having a low output impedance at D.C.

and said means coupled to said sensing electrodes for detecting signals generated by particles passing through said aperture having a low input impedance at the frequencies of the particle-generated signals, said circuitry including circuit means for coupling said signal-detecting means, said electrical excitation current establishing means, and the voltage potential across said aperture in such a manner that the D.C. component of the excitation current flowing through said aperture is made to vary inversely proportional to slow changes of the steady state resistance of the resistance across said sensing electrodes through said aperture with voltage across said sensing electrodes remaining constant.

2. The circuitry according to claim 1 wherein said signal-detecting means comprises a current-sensitive amplifier.

3. The circuitry according to claim 1 wherein said means for establishing the electrical excitation current includes a direct current power supply.

4. The circuitry according to claim 1 wherein said means for establishing said electrical excitation current includes an alternating current power supply.

5. The circuitry according to claim 1 including means coupled to said signal-detecting means for monitoring the conductivity of the liquid containing particles and for altering the output signals from said signal-detecting means relative to changes in liquid conductivity thereby to render said output signals independent of liquid conductivity.

6. The circuitry according to claim 1 wherein said means for establishing electrical excitation current to said aperture includes a power electrode adjacent to each one of said sensing electrodes, a power supply connected in series with said power electrodes, circuit means coupled to said sensing electrodes and including a reference voltage source and a comparator which compares the voltage across said sensing electrodes through said aperture with the voltage from said reference source and feedback circuit means connected between the output of said comparator and said power supply for altering the output of said power supply to adjust for changes in the voltage across said sensing electrodes so as to maintain the voltage across said sensing electrodes equal to the voltage from on said reference voltage source.

7. The circuitry according to claim 6 wherein said signal-detecting means includes a low input impedance amplifier connected between one of said power electrodes and said power supply.

8. The circuitry according to claim 6 wherein said signal-detecting means includes an amplifier connected across said sensing electrodes, said amplifier having a low input impedance at the frequencies of the particlegenerated signals, and a high impedance at D.C.

9. The circuitry according to claim 6 wherein said feedback loop comprises an R - C filter, a chopper-inverter, an A.C. power amplifier and a transformer connected in series between said comparator and said power supply.

10. The circuitry according to claim 1 wherein said means for establishing an electric excitation current includes an A.C. power supply and an inductance in series with said sensing electrodes and said signal-detecting means includes a capacitance and a low impedance amplifier in series with said sensing electrodes.

11. The circuitry according to claim 5 wherein said conductivity monitoring means includes a conductivity cell comprising two electrodes situated in the liquid in which one of said sensing electrodes is situated.

12. The circuitry according to claim 11 wherein the output of said signal-detecting means is connected to a modulator which modulates the output signal with a high frequency carrier, a current output stage connected to said modulator, and a demodulator, said current output stage having an output connected to one of said conductivity cell electrodes and to said demodulator, the other of said conductivity cell electrodes being connected to a common conductor for said circuitry.

13. The circuitry according to claim 5 wherein said conductivity monitoring means includes conductivity cell which is physically isolated from the sensing zone including said sensing aperture.

14. The circuitry according to claim 11 wherein said conductivity cell is long and narrow with each of said conductivity cell electrodes being located at one end of said cell.

15. The circuitry according to claim 14 wherein said conductivity cell includes a serpentine tubing communicating with the liquid in which said one sensing electrode is situated and said conductivity cell electrodes being located at either end of said tubing and communicating with the electrolyte within said tubing.

16. The circuitry according to claim 15 including a third electrode which constitutes one of said conductivity cell electrodes and which is located in said tubing intermediate the ends thereof and wherein said end electrodes together constitute the other of said conductivity cell electrodes and are connected together and to the common conductor for said circuitry.

17. The circuitry according to claim 1 wherein said electric current excitation establishing means includes an A.C. source, a first inductance and a first capacitance connected in series and said signal-dectecting means includes a second capacitance and a second inductance connected in series with said sensing electrodes and said electric current excitation establishing means, and said signal detecting means further includes a transformer the primary winding of which constitutes said second inductance, a low impedance amplifier connected to the secondary winding of said transformer, a frequency changer having a high output impedance connected to the output of said amplifier, and a conductivity cell formed between one of said sensing electrodes and a third electrode, the output of said frequency changer being connected to said third electrode and to a demodulator such that the output signal from said demodulator is independent of the aperture diameter and independent of the conductivity of the liquid containing the particles.

18. The circuitry according to claim 11 wherein said electric current citation establishing means includes a low impedance power source and said signal-detecting means includes a low impedance amplifier, said power supply and said amplifier being connected in series between one sensing electrode and a common conductor for said circuitry, the other sensing electrode being connected to said common conductor and forming one electrode of said conductivity cell, the other conductivity cell electrode being connected to the input of a tuned amplifier, an A.C. source and a capacitor connected in series between said common conductor and said input of said tuned amplifier, a multiplier having two inputs and an output, a rectifier filter connected between said tuned amplifier output and one of said multiplier inputs and the output of said low impedance amplifier being connected through a capacitance to the other multiplier input which input is also connected to a load resistance connected to said common conductor.

19. Electrical sensing circuitry for a particle-analyzing device wherein liquid containing particles is caused to flow through a sensing aperture on either side of which is located a sensing electrode, said circuitry including means coupled to said electrodes for establishing an electric excitation current through said aperture, means coupled to said electrodes for detecting signals generated by particles passing through said aperture and electrical monitoring means coupled to said signal-detecting means for monitoring the conductivity of the liquid containing particles and for electrically altering the output signals from said signaldetecting means relative to changes in the liquid conductivity, said circuitry including a modulator, the output of said signal detecting means being connected to said modulator which superimposes the output signals on a carrier frequency, said modulator having a current output stage coupled to a demodulator, and said conductivity monitoring means including a pair of conductivity sensing electrodes forming a conductivity cell in the liquid containing particles, said conductivity cell being connected to the input of said demodulator whereby the particle-generated signals on the carrier frequency at the input to the demodulator are simultaneously applied to a load resistance dependent upon conductivity of the liquid so that the output signals from said demodulator are independent of liquid conductivity.

20. Electrical sensing circuitry for a particle-analyzing device wherein liquid containing particles is caused to flow through a sensing aperture on either side of which is located a sensing electrode, said circuitry including means coupled to said electrodes for establishing an electric excitation current through said aperture, means coupled to said electrodes for detecting signals generated by particles passing through said aperture and electrical monitoring means coupled to said signal-detecting means for monitoring the conductivity of the liquid containing particles and for electrically altering the output signals from said signaldetecting means relative to changes in the liquid conductivity thereby to render said output signals independent of liquid conductivity, said circuitry further including a modulator, the output of said signaldetecting means being connected to said modulator which superimposes said output signals on a carrier frequency, said modulator having a current output stage coupled to the input of a demodulator through the primary of a transformer and an inductance, a capacitor being connected between said demodulator input and the common conductor for said circuitry, and said conductivity monitoring means including a conductivity cell defined by two electrodes situated in the liquid in which one of said sensing electrodes is situated, said conductivity cell being connected across the secondary of said transformer.

21. Electrical sensing circuitry for a particle-analyzing device wherein liquid containing particles is caused to flow through a sensing aperture on either side of which is located a sensing electrode, said circuitry including means coupled to said electrodes for establishing an electric excitation current through said aperture, means coupled to said electrodes for detecting signals generated by particles passing through said aperture and electrical monitoring means coupled to said signal-detecting means for monitoring the conductivity of the liquid containing particles and for electrically altering the output signals from said signaldetecting means relative to changes in the liquid conductivity thereby to render said output signals independent of liquid conductivity, and wherein said signal-detecting means includes an amplifier, and a first capacitance and a first resistance connected across said electrodes, the junction between said first capacitance and said first resistance being connected to the input of said amplifier, and said conductivity monitoring means including said sensing electrodes, a second resistance and a second capacitance connected across said sensing electrodes, and a divider for coupling said conductivity monitoring means to said signal-detecting means, the output of said amplifier being connected to the numerator input of said divider and the junction between said second resistance and said second capacitance being connected to the denominator input of said divider.

22. Electrical sensing circuitry for a particle analyzing device wherein liquid containing particles is caused to flow through a sensing aperture on either side of which is located a sensing electrode, said circuitry including means coupled to said electrodes for establishing an electric excitation current through said aperture, means coupled to said electrodes for detecting signals generated by particles passing through said aperture and electrical monitoring means coupled to said signal-detecting means for monitoring the conductivity of the liquid containing particles and for electrically altering the output signals from said signal detecting means relative to changes in the liquid conductivity thereby to render said output signals independent of liquid conductivity, and wherein said signal-detecting circuit includes a capacitor and a resistance connected across said electrodes and an amplifier connected to the junction between said capacitor and resistance, and said conductivity monitoring means includes said sensing electrodes, an oscillator and a capacitor connected in series across said electrodes, a capacitance and a inductance series tuned to the frequency of said oscillator and connected between the output of said amplifier and the common conductor for said circuitry, and a divider for coupling said conductivity monitoring means to said signal-detecting means, the junction between said capacitance and inductance being connected through a phase-sensitive filter to the denominator input of said divider and the output of said amplifier being connected to the numerator input of said divider.

23. Electrical sensing circuitry for a particle-analyzing device wherein liquid containing particles is caused to flow through a sensing aperture on either side of which is located a sensing electrode, said circuitry including means coupled to said electrodes for establishing an electric excitation current through said aperture, means coupled to said electrodes for detecting signals generated by particles passing through said aperture and electrical monitoring means coupled to said signal-detecting means for monitoring the conductivity of the liquid containing particles and for electrically altering the output signals from said signal-detecting means relative to changes in the liquid conductivity thereby to render said output signals independent of liquid conductivity, said means for monitoring conductivity including a conductivity cell defined by a pair of conductivity sensing electrodes in the liquid, said conductivity cell forming a resistance which is connected as a load resistance to the output of said signal-detecting means, and wherein said conductivity cell is physically isolated from the sensing zone including said sensing aperture.

24. The circuitry according to claim 23 wherein said conductivity cell is long and narrow with each of said conductivity cell electrodes being located at one end of said cell.

25. The circuitry according to claim 24 wherein said conductivity cell includes a serpentine tubing communicating with the liquid in which said one sensing electrode is situated and said conductivity cell electrodes being located at either end of the tubing and communicating with the electrolyte within said tubing.

26. The circuitry according to claim 25 including a third electrode which constitutes one of said conductivity cell electrodes and which is located in said tubing intermediate the ends thereof and wherein said end electrodes together constitutes the other of said conductivity cell electrodes and are connected together and to the common conductor for said circuitry.

27. In a particle study device wherein a liquid electrolyte containing particles is caused to traverse an electrical sensing zone of small dimensions and wherein said device has a conductivity cell including two electrodes in the electrolyte for establishing a variable resistance which is the function of the conductivity of the electrolyte and which is connected to electrical sensing circuit including the sensing zone to provide compensation for changes in electrolyte conductivity, the improvement comprising said conductivity cell including a long and narrow column of electrolyte between said electrodes with each of said electrodes being in contact with the electrolyte at one end of said column.

28. The conductivity cell according to claim 27 including a length of serpentine tubing and wherein said long and narrow column of electrolyte is defined by the electrolyte within said serpentine tubing, said electrodes being located at each end of said tubing and being in contact with the electrolyte in said tubing.

29. The conductivity cell according to claim 28 including a third electrode which constitutes one of said conductivity cell electrodes and which is located in said tubing intermediate the ends thereof and wherein said end electrodes together constitute the other of said conductivity cell electrodes and are connected together and to the common conductor for said circuitry.

30. The particle study device according to claim 27 wherein said conductivity cell is physically isolated from the sensing zone.

* * * * *